United States Patent [19]

Tona-Serra

[11] Patent Number: 5,505,914
[45] Date of Patent: Apr. 9, 1996

[54] DEVICE FOR OZONIZING SMALL AREAS OR SURFACES FOR THERAPEUTIC PURPOSES

[76] Inventor: Jaime Tona-Serra, Calle Montserrat, E-08519 Calldetenes (Barcelona), Spain

[21] Appl. No.: 376,952

[22] Filed: Jan. 20, 1995

[30] Foreign Application Priority Data

Jan. 20, 1994 [ES] Spain ........................... 9400110

[51] Int. Cl.⁶ .................................................. B01J 19/12
[52] U.S. Cl. ................ 422/186.12; 422/186.07; 422/906; 422/907
[58] Field of Search .................... 422/186.12, 186.07, 422/906, 907; 204/116

[56] References Cited

U.S. PATENT DOCUMENTS

| | | | |
|---|---|---|---|
| 1,071,109 | 8/1913 | Stiriz | 422/186.07 |
| 1,505,669 | 8/1924 | Quain | 422/186.07 |
| 4,021,921 | 5/1977 | Detaille | 32/40 R |
| 4,595,838 | 6/1986 | Kerschgens | 250/504 R |
| 4,743,199 | 5/1988 | Weber et al. | 433/216 |
| 4,776,515 | 10/1988 | Michalchik | 239/3 |
| 5,154,895 | 10/1995 | Moon | 422/186.07 |
| 5,381,789 | 1/1995 | Marquardt | 128/202.25 |
| 5,407,639 | 4/1995 | Watanabe et al. | 422/186.07 |
| 5,409,841 | 4/1995 | Chow | 436/180 |

*Primary Examiner*—Donald P. Walsh
*Assistant Examiner*—Daniel Jenkins
*Attorney, Agent, or Firm*—Kenyon & Kenyon

[57] ABSTRACT

A device for ozonizing small areas or surfaces for therapeutic purposes is provided having a first laminar element including a polyimide film, a similarly shaped second laminar element formed of fiberglass and polytetrafluroethylene, and a third smaller, flexible, conductive gold, silver or copper laminar element which is disposed between the first and second laminar elements. A signal of sufficient strength produces a number of electrical microdischarges between the device and the surface or area to which it is applied, with mass (ground) return, thereby producing an allotropic effect over the local oxygen, which is ionized together with the entire area to which the device is applied.

5 Claims, 1 Drawing Sheet

DEVICE FOR OZONIZING SMALL AREAS OR SURFACES FOR THERAPEUTIC PURPOSES

FIELD OF THE INVENTION

The present invention relates to a device for ozonizing small areas or surfaces for therapeutic purposes.

More particularly, the present invention relates to an electronic device comprising a series of laminas, that is capable of ozonizing small areas or surfaces by an electrical microdischarge in response to a signal.

BACKGROUND INFORMATION

Several different therapeutic devices for the treatment of different diseases are known, such as the application of heating elements to different parts of the body to treat arthritis, and also radiation treatments for many different kinds of diseases.

SUMMARY OF THE INVENTION

A device for ozonizing small areas or surfaces for therapeutic purposes according to the present invention comprises:

(a) a first variably shaped laminar element that includes, for example, a surface formed of a polyamide film, which may be formed by the condensation of a tetrabasic aromatic acid with an aromatic diamine, to which is attached (b) a second similarly shaped laminar element that includes, for example, a surface formed of fiberglass and polytetrafluroethylene; and (c) a third smaller lamina, which is disposed between the first laminar element and the second laminar element, and which is formed of, for example, gold, silver or copper, to which a conductive lead is attached.

The laminar elements may have different shapes, depending on the intended use and on the support element used, but maintaining a free surface. An adhesive, for example, a silicone adhesive, may be used for attaching the laminar elements to each other.

The above-described device may be applied to an area to be treated with the surface on which the polyamide film is found facing the area to be treated, although either surface may be used, depending on the condition that is to be treated. Through the conductive lead attached to the third laminar element, a signal of appropriate strength can be transmitted to induce a number of electrical microdischarges on the surface to which the device is applied, with mass (ground) return. This produces an allotropic affect over the local oxygen, such that this oxygen is ozonized, as is the entire zone of application.

By carefully controlling the strength of the signal which is applied to the device, it is possible to go beyond ozonization of the immediate area to the production of a slight superficial heat. A greater amount of heat may be produced if the side of the device on which the fiberglass surface is found fares the treated area.

Due to the therapeutic effect of ozone, the present invention can be used for dermatological, surgical, traumatological, rheumatological and other therapies, for comparable veterinary applications, and also for ecological applications.

The device according to the present invention may also include a microsensor to measure certain parameters (e.g., temperature, humidity, etc.), which may be located on any of the elements of the device.

DETAILED DESCRIPTION OF THE INVENTION

Figure 1:
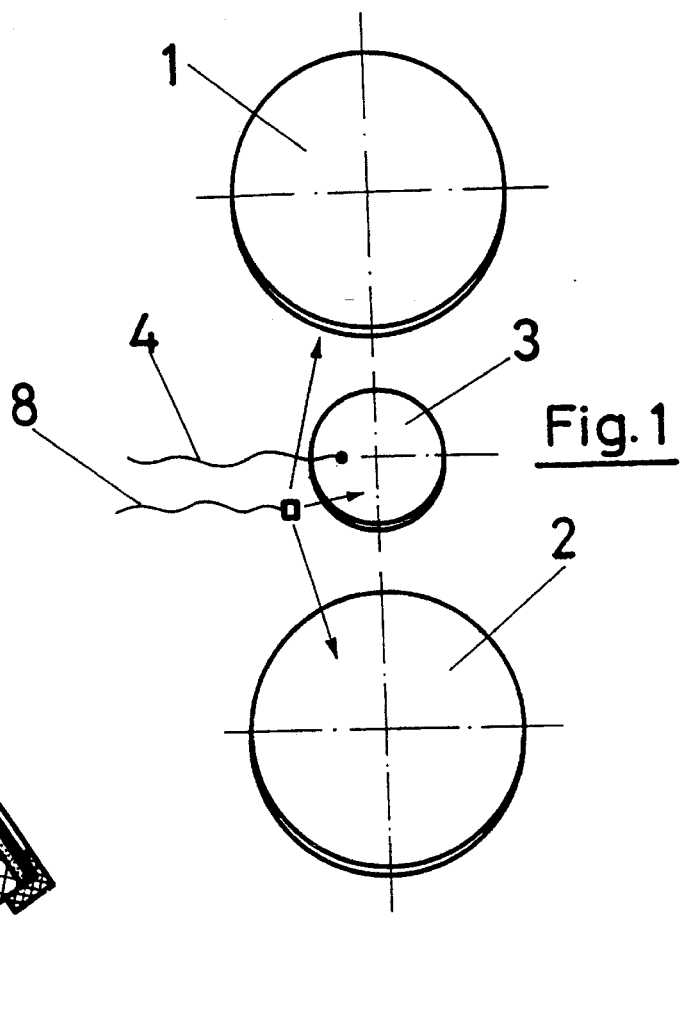
FIG. 1 shows a schematic drawing of a device for ozonizing small areas or surfaces according to the present invention.

FIG. 1 illustrates an example of a device according to the present invention for ozonizing small areas or surfaces for therapeutic purposes. The device includes: a variably shaped first laminar element 1 which may have a first surface formed of, for example, a polyimide film; and a second similarly shaped laminar element 2 formed of, for example, fiberglass with polytetrafluroethylene, adhesively connected to the first laminar element 1 via, for example, a silicone adhesive; and also a third smaller laminar element 3 located between elements 1 and 2. The third element 3 is formed of, for example, a flexible, conductive gold, silver or copper lamina to which is attached a conductive lead 4 through which a signal of adequate strength may be applied. The polyimide film of element 1 may be obtained by the condensation of tetrabasic aromatic acids with an aromatic diamine, to yield the surface that is applied to the zone (area) to be treated.

The use of the device according to the present invention involves positioning the surface of the first laminar element 1 adjacent to the area to be treated (although either surface may be used, depending on the diseased state that is to be treated), and then supplying to the device, through its lead 4, a signal of sufficient strength to produce a number of electrical microdischarges between said device (comprised of superimposed laminar elements 1, 2 and 3) and the application zone, with mass (ground) return, thereby producing an allotropic affect on the adjacent oxygen, which is ozonized together with the zone of application.

Another embodiment of the present invention includes the use of a signal of reduced radio-frequency which produces a localized, slight superficial heat, or more heat if the device is applied through the fiberglass surface of the second laminar element.

The present invention may also include a microsensor 8 capable of measuring certain parameters (e.g., temperature, humidity, etc.), that may be located on any of the elements of the device.

For most applications, the embodiment of the present invention including only the three laminar elements 1, 2 and 3 is sufficient, to thus take advantage of its flexibility. However, in certain instances it may be useful to further include a support framework to provide greater maneuverability during application of the device.

Figure 2:
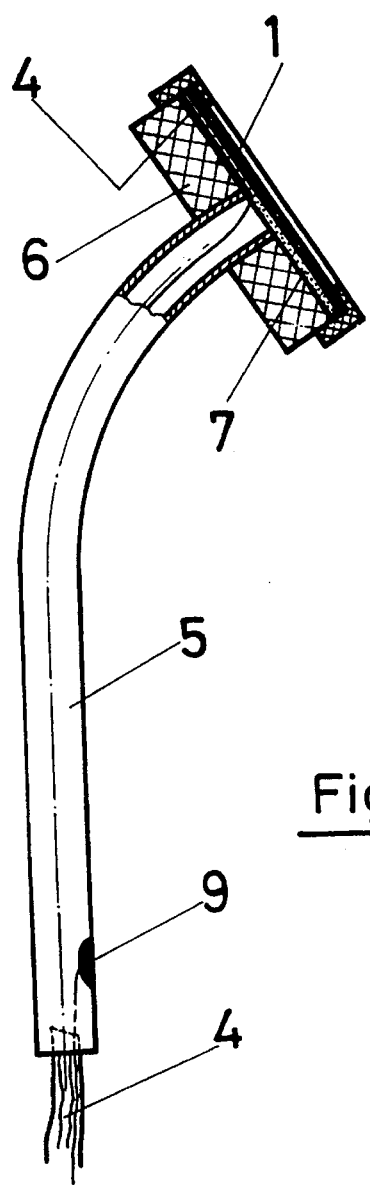
FIG. 2 illustrates an exemplary support element that may be used with the device according to the present invention.

FIG. 2 illustrates another embodiment of the present invention, wherein a support structure facilitates the comfortable maneuvering of the embodiment shown in FIG. 1, wherein said support structure comprises a handle 5 which terminates in a circular element 6 and an additional element 7 formed of a foam or of a similar material. The handle 5 has a hollow core or conduit which can house the lead 4 through which the above mentioned signal may be transmitted to the device according to the present invention, and also a connection 9 connected to the metallic part of the handle, so that this handle may function as a return circuit in applications that require it (e.g. autoapplication, etc.)

What is claimed is:

1. A device for ozonizing a small area or surface, comprising:
   (a) a first laminar element having a surface formed of a polyimide film;
   (b) a second laminar element having a surface formed of a fiberglass and a polytetrafluroethylene;
   (c) a third laminar element disposed between the first laminar element and the second laminar element, the third laminar element being smaller than the first laminar element and the second laminar element, a conductive lead being connected to the third laminar element;
   wherein one of the surface of the first laminar element and the surface of the second laminar element of the device is placed next to an area to be treated and a signal is transmitted through the conductive lead, the conductive lead having a ground return, the signal being sufficient to produce a number of electrical discharges between the area to be treated and the device, thereby producing an allotropic affect over adjacent oxygen such that the adjacent oxygen and the area to be treated is ozonized.

2. A device for ozonizing a small area or surface according to claim 1, wherein the laminar elements are adhesively attached via a silicone adhesive.

3. A device for ozonizing a small area or surface according to claim 1, wherein the third laminar element includes a flexible, conductive lamina of one of gold, silver and copper.

4. A device for ozonizing a small area or surface according to claim 1, wherein the first laminar element has a first predetermined shape, the second laminar element has a second predetermined shape similar to the first predetermined shape, and the third laminar element has a shape smaller than the first and second predetermined shapes.

5. A device for ozonizing a small area or surface according to claim 1, further comprising a microsensor capable of measuring a predetermined parameter, wherein said microsensor is attached to one of the first laminar element, the second laminar element and the third laminar element.

* * * * *